(12) United States Patent
Kharkwal et al.

(10) Patent No.: US 6,449,899 B1
(45) Date of Patent: Sep. 17, 2002

(54) **METHOD FOR INDUCING IMPROVED SEED GERMINATION IN *PODOPHYLLUM HEXANDRUM* ROYLE**

(75) Inventors: Amit Chandra Kharkwal, Palampur (IN); Om Prakash, Palampur (IN); Amita Bhattacharya, Palampur (IN); Pramod Kumar Nagar, Palampur (IN); Paramvir Singh Ahuja, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/800,672

(22) Filed: Mar. 8, 2001

(51) Int. Cl.⁷ ................................................. A01G 1/00
(52) U.S. Cl. ............................. 47/58.1 SE; 47/58.1 FV
(58) Field of Search ....................... 47/58.1 R, 58.1 SE, 47/58.1 FV

(56) References Cited

U.S. PATENT DOCUMENTS

| | | | | |
|---|---|---|---|---|
| 5,705,508 A | * | 1/1998 | Ojima et al. | 514/320 |
| 5,750,709 A | * | 5/1998 | Castor | 546/348 |
| 5,856,351 A | * | 1/1999 | Zheng et al. | 514/450 |

* cited by examiner

Primary Examiner—Charles T. Jordan
Assistant Examiner—Jeffrey L. Gellner
(74) Attorney, Agent, or Firm—Burns, Doane, Swecker & Mathis, L.L.P.

(57) ABSTRACT

The present invention describes a method for inducing improved seed germination in a high altitude medicinal plant, *Podophyllum hexandrum* Royle through hot water treatment at 40° C.–100° C. for 30–120 seconds.

15 Claims, No Drawings

METHOD FOR INDUCING IMPROVED SEED GERMINATION IN *PODOPHYLLUM HEXANDRUM* ROYLE

FIELD OF THE INVENTION

The present invention relates to a method for inducing improved seed germination in a high altitude, medicinal and endangered plant, *Podophyllum hexandrum* Royle

BACKGROUND OF THE INVENTION

*Podophyllum hexandrum* Royle is an important medicinal plant, which grows in the inner ranges of Himalayas at an altitude of 2700–4200 m from Kashmir to Sikkim (Badhawar and Sharma 1963), extending up to south west of China.

The rhizomes of *Podophyllum hexandrum* are rich in podophyllotoxins and have anticancer and antitumor properties (Kamil and Dewick, 1986). The podophyllotoxins are lignans whose semi-synthetic derivatives-etoposide (VP-16-213) and teniposide (VM-26) are approved drugs for the treatment of testicular and lung cancer (Stahelin and Warburg, 1991). *P. hexandrum* has the maximum podophyllotoxins up to about 4% from dried roots as compared to 0.25% of *P. peltatum* (Jackson and Dewick, 1984a).

Ever increasing demand for this drug in modern medicine, coupled with its existing use in traditional system of medicine has resulted in ruthless uprooting of the underground parts of the plant leading to intense collection coupled with the lack of organized cultivation. Consequently, *P. hexandrum* has been declared as an endangered species (Airi et al., 1997, Bhadula et al., 1997), thus, expeditious methods are required for its sustained propagation and organized utilization. Moreover, since Podophyllum generally grows at high altitudes of the Himalayas and inaccessible locales, it is all the more essential to cultivate these plants in large numbers (Badhawar and Sharma, 1963) for their sustainable utilization.

Early attempts in domestication of Podophyllum were through multiplication of rhizomes. However, since rhizomes are also the source of podophyllotoxins, considerable loss is incurred either in terms of propagules (when uprooted) or important harvestable materials of pharmaceutical importance (when conserved) (Sadowska et al., 1997). The other infrequent method of propagation is through seed germination. Seed germination is erratic and is further limited by long periods of seed coat imposed or mechanical and endosperm dormancy which cannot be generally broken by traditional methods (Badhawar and Sharma, 1963). More than the germinability of the seeds, the structural barrier in the seedlings i.e. the hypocotyl (Purohit and Nautiyal, 1986) may also reduce the chances of its survival in nature (Nautiyal et al., 1987).

Thus, it is not surprising that despite the urgent necessity of mass propagation and conservation of Podophyllum, the work done till date has been limited only to academic interests with respect to the small number of plants propagated. The major objective in the propagation of endangered species is conservation of valuable heterogeneity. An improved method of uniform seed germination which also leads to successful field establishment will help in removal of existing problems which hinders successful plant establishment and large scale non-destructive propagation. The germinative propagation will also help in raising large scale population of heterogeneous plants of representative gene pool.

Reference may be made to the work of Troup, (1915) wherein he reported the (i) the presence of a dormancy period of about two to three years in the seeds that were collected immediately after fruit ripening (ii) sporadic germination which commenced after 3 months and continued up to 7 months of sowing (iii) failure to break the seed dormancy after soaking the seeds for 8 days in water (iv) rather sporadic and forced germination under abnormal conditions at an altitude of 660 m above mean sea level. A similar report of Bhadawar and Sharma (1963) wherein they also indicated the (i) the presence of a dormancy period of about 9–10 months in the seeds and poor germination of about 7–45% (ii) different treatments like soaking of seeds in luke warm water for 24 hrs, 60% $H_2SO_4$ for five minutes and chipping of seeds with a blade all failed to break seed dormancy and induce germination The drawbacks include (i) the reports does not provide a method for germination of seeds in large numbers (ii) the time taken for complete seed germination was relatively long (iii) seed germination was poor (iv) there is no mention of growth conditions required for seed germination and hence, the method cannot be reproduced (v) a long dormancy period of about 9–10 months which could not be overcome by any of the treatments tested; therefore, the time required for seed germination could not be shortened (vii) the treatments that were employed for breaking seed dormancy were not effective.

Rust and Roth, (1981) studied the seed production and seedling establishment in the other related species—*Podophyllum peltatum* wherein they found that under natural conditions in 14 hectares of Quercus-Liriodendron forest that was cut 90 years ago, the seeds planted below ground showed 24.4±3.2% germination with very high seedling mortality rate (98.7%). The major objective of this paper was to study seed production potential and seedling establishment under natural conditions so as to study the natural processes controlling seed germination and seedling establishment. The drawbacks are (i) poor seed germination (24.4%) and (ii) seedling mortality rate beyond acceptable limits.

Reference may be made to Nautiyal et al., (1987), wherein no germination of fresh seeds at 20° C. as compared to 66% and 88% germination in seeds stored for one month at low temperatures with and without Gibberellic acid treatment respectively. The drawbacks are (i) no germination of fresh seeds (ii) requirement of one month of low temperature storage prior to germination (iii) time required for seed germination is considerably long and (iv) germination even after storage was comparatively low.

Reference may be made to Choudhary et al., (1996) wherein relatively poor germination of 3 months old sterilized seeds on moistened filter papers in Petri dishes at room temperature (10–22° C.) under light and dark conditions with and without scarification. While under dark conditions, scarified seeds germinated (60.0%) after 45–60 days of sowing, very poor (8.89%) germination under light conditions was achieved. In non scarified seeds up to 78.88% and 14.44% germination under light and dark condition was reported after 120 days of seed sowing. The drawbacks are (i) the method described is cumbersome and long (ii) time required for seed germination under all conditions is long, (iii) cumbersome and labour intensive methods like scarification are required (iv) data on seed germination at room temperature makes it a non-reproducible and unsatisfactory because of the fluctuations in physical parameters, (v) maximum germination is relatively poor i. e. 78.88% and (vi) there is no mention of field establishment of seedlings.

Reference may be made to Choudhary et al., (1998) wherein the cultivation method for *P.hexandrum* through seeds is described. Following their previous method for seed germination, seedling development and true leaf emergence (4 months after seed germination) under natural conditions is reported. The drawbacks are (i) the previous protocol which was employed for germination and seedling establishment was very long and cumbersome, (ii) rate of seed germination under recommended cultural practices is not reported, (ii) the actual percent or the number of seedlings that were transferred has not been reported, (iii) seedling mortality rate which is very crucial for its survival has not been mentioned and, (iv) details about the actual percent or number of true leaf emergence was not given.

Reference may be made to Singh et al., (1999) wherein the seed germination behaviour among different populations of P. hexandrum. Under controlled conditions, up to 95% seed germination was reported in the alpine seeds at 30° C. under light after 100 days of sowing. The germination tests were performed on filter paper in Petri dishes. The drawbacks are (i) seed germination took a long time i.e. up to 100 days (ii) the method reported deals with germination of alpine seeds only (iv) the method reported deals with germination of seeds on filter papers and not in soil (v) emergence of true leaves has not been mentioned (vi) seedling mortality rate is a major factor limiting germinative propagation of Podophyllum (Rust and Roth, 1981) however, no mention has been made regarding this (vii) the reported method requires cumbersome treatments like drying of seeds for one week at room temperature followed by storage at 4–6° C. in moist polythene bags prior to germination and (viii) statistically significant results were not presented in such a large massive scale study which started during 1987 and continued till 1990.

Recently, Nadeem et al., (2000) also reported seed germination of P. hexandrum, wherein germination started nearly 3 months after sowing and was enhanced 5-fold by treatment with sodium hypochlorite and two fold by treatment with either Gibberellic acid (250 mM) alone or in combination with benzyladenine (250 mM). The major drawbacks include (i) long time period (3 months) required for start of seed germination (ii) no mention of true leaf emergence.

GardenBed.com, a website also provides cultivation notes on propagation of P. hexandrum under the caption 'Plants for a future' wherein seeds stored in a cold frame are sown in dark cold frame in March. Seeds start germinating after 1–4 months at 15° C. The drawbacks are (i) requirement of seed storage at low temperature, (ii) long time period (1–4 months) required for start of seed germination and (ii) no mention of true leaf emergence.

OBJECTS OF THE INVENTION

The main object of the present invention is to provide a method for inducing improved seed germination at high altitudes, in a medicinal and endangered plant, Podophyllum hexandrum Royle.

Another object of the invention is to raise heterogeneous populations of Podophyllum hexandrum Royle so as to maintain the maximum genetic diversity which may be below the species level.

Still another object of the invention is to transfer the ex situ raised plants to the in situ conditions.

Yet another object of the invention is to shorten the life cycle of the plants significantly.

Another object of the invention is to specify the potting mix required.

Yet another object of the present invention is to specify the growth conditions required for the plants of Podophyllum hexandrum.

Still another object of the present invention is to provide characterized planting materials.

Another object of the present invention is to obviate the costly, time consuming and labour intensive methods of breaking seed dormancy and thereby making the present method cost, time, and labour effective.

DETAILED DESCRIPTION OF THE INVENTION

Accordingly the present invention provides a method for inducing improved seed germination at high altitudes in an endangered medicinal plant, Podophyllum hexandrum Royle, said method comprising the steps of:

(a) collecting mature pods of P. hexandrum Royle,
(b) separating the seeds from the pulp,
(c) disinfecting the seeds with 0.1% Bavistin and 1% streptomycin sulphate for 15 minutes,
(d) treating the fresh seeds with hot water ranging from 40–100° C. for varied time intervals ranging from 30–120 seconds,
(e) sowing the hot water treated seeds in pots containing sand:soil:farm yard manure in the ratio 2:1:1 at a depth of ½ inch,
(f) maintaining the sown seeds in the pots at a minimum of 30° C. during day and at least 20° C. during night and relative humidity of 60–70%, and
(g) sprinkling water at least once after every two days.

The plant Podophyllum hexandrum is collected from their natural habitats in the Western Himalayas at an altitude ranging from 2700 m–3500 m above mean sea level during the first week of September. In an embodiment, Podophyllum hexandrum seeds from different regimes of Himachal Pradesh, a state in India, can be used. Immediately after collection of the seeds, the seeds are separated from the pulp.

Once the seeds are hot-water treated, they are sown in 8" pots. In another embodiment various chemicals like HCl (0.5–1N), $H_2SO_4$ (0.5–1N) acetone (25–100 mM), potassium nitrate (50–150 mM), and polyethyleneglycol solution (10–40%) and its mix with dry sand at different concentrations were used for inducing seed germination Further, after the seeds sown in the pots are allowed to mature in green or poly-houses at temperatures as said earlier. In the present invention, this was done at the laboratory at Palampur, India, which is 1210 m above mean sea level.

In yet another embodiment seeds were scarified and given the following treatments: a minimum of 4° C. in moist sand for 1–4 weeks, gibberrellic acid treatment (5–20 mg/l for a minimum of 30 minutes), potassium nitrate (50–150 mM) for at least 30 minutes and 25° C. in moist sand for 1–4 weeks.

In still another embodiment seeds were stratified and kept at a minimum of 4° C. in moist sand for 1–4 weeks and 25° C. in moist sand for 1–4 weeks.

In still another embodiment seeds were treated with Gibberrellic acid (5–20 mg/l for 30 minutes).

The seeds were treated with hot water ranging from 40, 60, 80 and 100° C. for 30, 60, 90 and 120 seconds. Different combinations of sand soil and farm yard manure (3:1:1, 2:1:1, 1:1:1, 1:3:1 and 1:2:1) were tested for sowing the seeds for germination. Different depths (½, 1 and 2 inches) required for sowing the seeds were standardized in different containers like Hikkotrays, 4", 8" pots and beds containing potting mix in poly tunnel. Interval for watering (at least once in 1, 2, 3 days) of the pots containing sown seeds were standardized.

(i) This invention specifies the green or poly-house conditions (30° C. during day alternating with 20° C. during night with 60–70% relative humidity) required for plant establishment, true leaf emergence and healthy growth of plants.

(ii) This invention specifies the transfer of green or poly-house grown plants to their natural habitat.

(iii) It is the most efficient method for the highest percentage (up to 90%) of field establishment and survival of *P. hexandrum* seedlings.

(iv) It minimizes the time period for seedling establishment from 11 months(Rust and Roth 1981) to 4 years (Singh et al., 1999) to 4 months only.

A number of treatments like temperature, chemical, hormonal and mechanical treatments have been successfully employed for breaking the dormancy of many seeds and for achieving uniform germination. Since *P. hexandrum* plants are high altitude plants, the likelihood of the life of the seeds being regulated by temperature is high. The thermo-opportunistic behaviour of these seeds has also been reported earlier by Singh et al., (1999). Germination only at a particular season i.e. summer under natural conditions at high altitudes led us to hypothesize the probable requirement of relatively higher temperature as an important requirement for germination of these seeds. Moreover the presence of endosperm dormancy in these seeds as reported by earlier workers (Arumugum and Bhojwani, 1989) indicate the presence of certain chemical or hormonal inhibitors. The present invention uses excised embryo culture which also proves the fact that removal of inhibitory covers results in successful germination. The success obtained after a quick treatment with hot water at 40° C.–100° C. for 30–120 seconds therefore, suggest that (i) either the embryo loses its sensitivity to the inhibitors that are present in the endosperm and/or seed coat (ii) the structural barriers imposed by the seed coat is overcome by the embryos when hot water treatment softens the seed coat. This is further proven by the results that were obtained with treatments for: (a) seed coat softening with chemicals like HCl, $H_2SO_4$, acetone and (b) seed coat removal like scarification and embryo culture technique and (c) involving the induction of physiological changes in the embryos like making them insensitive to inhibitors or antagonising the inhibitory effects with the promotory hormones like Gibberellic acids and chemicals like Potassium nitrate, Polyethylene glycol etc. Although these treatments are not as effective as hot water treatments, yet they indicate the presence of both structural and endosperm dormancy. Only 8" long pots were selected because roots of this plant grows extensively during this period and attain a length of 6–8 cm after 60 days of sowing and 8–12 cm after 120 days of sowing. The ratio of the potting mix was standardized keeping in view the type of soil found in this area which is clayey and is depleted in some nutrients. To keep the potting mix porous two parts of sand was added and to retain the moisture one part soil was added. To augment mineral and organic nutrients one part farm yard manure was also added.

In other words, the present invention describes a method for inducing improved seed germination in a high altitude medicinal plant, *Podophyllum hexandrum* Royle through hot water treatment at 40° C.–100° C. for 30–120 seconds. Seed germination commenced after 30 days of seed sowing in potting mix under green house. Up to 100% seed germination was achieved within 70 days of seed sowing. True leaf emergence to the extent of 40% was also achieved within 90 days of seed sowing. Very high seedling survival percent (90%) was achieved after 120 days of seed sowing. This method facilitates mass propagation of *Podophyllum hexandrum* coupled with successful field establishment and early emergence of true leaves due to specific growth conditions and potting mix. This method thus enables (i) the transfer of ex situ raised plants to their natural habitat (ii) raising heterogeneous population (iii) raising characterized planting material for ensuring traceability (iv) domestication of plants in places other than their natural habitat (v) shortening the natural life cycle of the plant.

The following examples are given by way of illustration and therefore should not be construed to limit the scope of the present invention.

EXAMPLES

Example-1

Freshly harvested seeds in first week of September were treated with hot water at 40–100° C. for 30–120 seconds. The treated seeds were sown in the 8" pots containing sand:soil:farm yard manure (2:1:1).The pots were kept in a green or poly-house of IHBT Palampur (1210 m above mean sea level) maintained at a minimum 30° C. during day and at least 20° C. during night with 60–70% Relative Humidity. Water was sprinkled on pots once every two days. Germination of seeds started after 30 days of sowing and after 70 days up to 100% seed germination was achieved. Up to 40% true leaf emergence was achieved after 90 days of seed sowing and more than 90% survival and plant establishment were recorded after 120 days of sowing. The seedlings were transferred to their natural habitat in the month of August in the following year.

Example-2

Various chemicals like HCl (0.5–1 N), $H_2SO_4$ (0.5–1 N) acetone, potassium nitrate (50–150 mM), and polyethyleneglycol-6000 solution at different concentrations (10–40%) and its mix with dry sand were used for inducing seed germination. Germination of seeds started after 35 days of sowing and after 70 days up to 90% seed germination was achieved. Up to 30% true leaf emergence was achieved after 90 days of seed sowing and more than 90% survival and plant establishment was recorded after 120 days of sowing.

Example-3

Seeds were scarified and given the following treatments: 4° C. in moist sand for 1–4 weeks, Gibberellic acid treatment (5–20 mg/l for 30 minutes), potassium nitrate (50–150 mM) for 30 minutes and 25° C. in moist sand for 1–4 weeks. Germination of seeds started after 30 days of sowing and after 70 days up to 80% seed germination was achieved. Up to 25% true leaf emergence was achieved after 90 days of seed sowing and more than 90% survival and plant establishment was recorded after 120 days of sowing.

Example-4

Seeds were stratified and kept at 4° C. in moist sand for 1–4 weeks and 25° C. in moist sand for 1–4 weeks. Germination of seeds started after 30 days of sowing and after 70 days up to 80% seed germination was achieved. Up to 30% true leaf emergence was achieved after 90 days of seed sowing and more than 90% survival and plant establishment was recorded after 120 days of sowing.

Example-5

Seeds were collected from different regimes of Himachal Pradesh and were germinated as described above with up to 100% germination within 70 days, 40% true leaf emergence within 90 days and 90% field survival after 120 days of seed sowing.

The Main Advantages of the Present Invention Are

1) This is the first defined method for circumventing the mechanical removal of seed dormancy through scarification etc. during germination.

2) This is the first defined method for circumventing the mechanical removal of correlative inhibition of cotyledons for true leaf emergence thereby, ensuring mass scale propagation of plants. The present invention employs hot water treatment prior to germination thereby, making it simple and most cost effective as compared to the reports where costly plant growth hormones likes Gibberellic acid and Benzyladenine have been employed.

3) This is the first defined method that does not require seed drying or low temperature storage for seeds prior to germination as fresh seeds excised from pods germinate up to 100% in soil.

4) This is the first defined method that does not require prior germination under laboratory conditions involving fluorescent light etc. and later their transplantation to the soil thereby, ensuring much lower mortality rates.

5) This method can work efficiently in all populations of *P. hexandrum* both from alpine and temperate regimes.

6) This is the first defined method wherein uniform seed germination, i.e. up to 100% can be achieved within 70 days of sowing.

7) This is the first defined method wherein true leaves start to emerge within 70 days and up to 40% emergence is achieved within 90 days.

8) This is the first defined method which does not require time consuming treatments involving manual labour and is hence, cost, time and labour effective.

9) This is the first defined method in which survival percentage of seedling is as high as 90% after 120 days of seed sowing.

10) This is the first defined method by which healthy plants could be successfully transferred to natural parks and reserves.

11) This invention by way of expediting the process of true leaf emergence ensures shortening the life cycle of plant by at least one season (8 months) as compared to what happens in nature. It also minimizes the time period for seedling establishment from 11 months (Rust and Roth 1981) and 4 years (Singh et al., 1999) respectively to 4–5 months only.

12) The present invention ensures statistically significant results for large-scale propagation of *Podophyllum hexandrum*.

13) The present method helps in domestication of plants in places other than their natural habitat.

14) The present method helps to raise heterogeneous population of *Podophyllum hexandrum* Royle as to maintain the maximum genetic diversity which may be below the species level.

15) The present method ensures the transfer of ex situ raised plants to in situ conditions.

16) The present method specifies the required potting mix.

17) This is the first defined method which enables the propagation of *Podophyllum hexandrum* Royle from both temperate and alpine regimes in regions where the day temperature is as high as 30° C. and the night temperature is 20° C. and the relative humidity is 60–70%.

This is a reproducible and defined method for uniform and large scale germination of *P. hexandrum* seeds as compared to all the above reports. The present method enables up to about 100% germination within 70 days. In the present invention, seeds are directly sown into the soil under green or poly- house condition therefore, the present method does not require germination first under laboratory conditions followed by transplantation. Thus, fluorescent lights and laboratory conditions are not required for seed germination as stated in the above reports. The method ensures successful field establishment of healthy plants coupled with very low mortality rate especially as it does not require transplantation steps. The method expedites the process of true leaf emergence to the extent of 40% within 90 days. This is in contrast to all the above reports wherein no true leaf emergence is achieved within such a short time or up to such high percent. This method by way of expediting the process of true leaf emergence ensures shortening the life cycle of plant by at least one season (8 months) as compared to what happens in nature; 11 months (Rust and Roth, 1981) to 4 years (Singh et al., 1999). The present method ensures statistically significant results for large-scale propagation of *Podophyllum hexandrum* as compared to all above reports. The present method is not confined to alpine seeds only and is successfully applicable to seeds of different regimes. The present method obviates the different cumbersome methods that have been employed for treating the seeds prior to germination. The present method enables the generation of up to 100% seedlings and 90% healthy plants that can be easily transplanted to different natural regimes. The present method obviates the requirement for seed drying prior to seed germination thus saving the time and labour. The present method obviates the requirement for storage of seeds for maximal germination as fresh seeds can result in up to 100% seed germination within 70 days. The present method offers a very simple process of breaking seed dormancy even in the field by hot water treatment at 40° C.–100° C. for 30–120 seconds and thus obviates all the costly and cumbersome treatments that have been employed in the above reports. The present method can make propagation under in situ condition relatively easier with uniform seed germination and early plant establishment with true leaf emergence.

The method of the invention ensures that ex situ raised plants could be transferred to their natural habitat The heterogeneous population of Pododphyllum could be raised to conserve genetic diversity, which may be below level of species. Characterized planting material would be provided to concerned pharmaceutical agencies under the new WTO trade regime to ensure traceability. Heterogeneous planting material would be provided to conservation parks and forest reserves to retain biodiversity. Domestication of plants in places other than their natural habitat has been ensured.

What is claimed is:

1. A method for inducing improved seed germination at high altitudes in an endangered medicinal plant, *Podophyllum hexandrum* Royle, said method comprising the steps of:

(a) collecting mature pods of *P. hexandrum* Royle, (b) separating the seeds from the pulp, (c) disinfecting the seeds with 0.1% carbendazim and 1% streptomycin sulphate for 15 minutes, (d) treating the fresh seeds with hot water ranging from 40–100° C. for varied time intervals ranging from 30–120 seconds, (e) sowing the hot water treated seeds in pots containing sand:soil:farm yard manure in the ratio 2:1:1 at a depth of ½ inch, (f) maintaining the sown seeds in the pots at a minimum of 30° C. during day and at least 20° C. during night and relative humidity of 60–70%, and (g) sprinkling water at least once after every two days.

2. A method as claimed in claim 1, wherein the method is repeatable for two successive years.

3. A method as claimed in claim 1 wherein the seeds are separated from their pulp immediately after collection.

4. A method as claimed in claim 1 wherein the seeds are sown in 8" pots containing the potting mix in poly-tunnel.

5. A method as claimed in claim 1 wherein the growth conditions for seed germination and seedling establishment and true leaf emergence are under green-house.

6. A method as claimed in claim 1 wherein the seeds after sowing are allowed to mature under green- or poly-house conditions in pots containing the potting mix in poly-tunnel.

7. A method for inducing improved seed germination at high altitudes in an endangered medicinal plant, *Podophyllum hexandrum* Royle, said method comprising the steps of:

(a) collecting mature pods of *P. hexandrum* Royle, (b) separating the seeds from the pulp, (c) disinfecting the seeds with 0.1% carbendazim and 1% streptomycin sulphate for 15 minutes, (d) treating the fresh seeds with hot water ranging from 40–100° C. for varied time intervals ranging from 30–120 seconds, (e) sowing the hot water treated seeds in container or beds containing a potting mix of sand, soil and farm yard manure at a depth of from ½ to 2 inches, (f) maintaining the sown seeds at a minimum of 30° C. during day and at least 20° C. during night and relative humidity of 60–70%, and (g) sprinkling water after every one to three days.

8. A method as claimed in claim 7, wherein the method is repeatable for two successive years.

9. A method as claimed in claim 7, wherein the seeds are separated from their pulp immediately after collection.

10. A method as claimed in claim 7, wherein the potting mix contains sand:soil:farm yard manure in the ratio 2:1:1.

11. A method as claimed in claim 7, wherein the hot water treated seeds are sown in the potting mix at a depth of ½ inch.

12. A method as claimed in claim 7, wherein the seeds are sown in 8" pots containing the potting mix in poly-tunnel.

13. A method as claimed in claim 7, wherein the growth conditions for seed germination and seedling establishment and true leaf emergence are under green-house.

14. A method as claimed in claim 7, wherein the seeds after sowing are allowed to mature under green- or poly-house conditions in pots containing the potting mix in poly-tunnel.

15. A method as claimed in claim 7, wherein the water is sprinkled at least once after every two days.

* * * * *